United States Patent [19]

Murphy

[11] Patent Number: 5,653,764
[45] Date of Patent: Aug. 5, 1997

[54] MODULAR HIP PROSTHESIS WITH DISCRETE SELECTABLE ANGULAR ORIENTATION

[76] Inventor: Stephen B. Murphy, 16 Cedar Rd., Chestnut Hill, Mass. 02167

[21] Appl. No.: 197,958

[22] Filed: Feb. 17, 1994

[51] Int. Cl.[6] ............................................. A61F 2/36
[52] U.S. Cl. ........................... 623/23; 623/11; 623/16; 623/18; 623/22
[58] Field of Search .................. 623/11, 16, 18–20, 623/22–23

[56] References Cited

U.S. PATENT DOCUMENTS

| | | |
|---|---|---|
| 4,051,559 | 10/1977 | Pifferi . |
| 4,608,055 | 8/1986 | Morrey et al. ............................ 623/23 |
| 4,795,469 | 1/1989 | Oh ............................................ 623/22 |
| 5,100,407 | 3/1992 | Conrad et al. ........................... 623/18 |
| 5,135,529 | 8/1992 | Paxson et al. ........................... 623/23 |
| 5,156,624 | 10/1992 | Barnes ...................................... 623/18 |
| 5,286,260 | 2/1994 | Bolesky et al. ........................... 623/18 |
| 5,405,403 | 4/1995 | Mikhail .................................... 623/18 |
| 5,413,610 | 5/1995 | Amino et al. ............................ 623/18 |

FOREIGN PATENT DOCUMENTS

| | | | |
|---|---|---|---|
| 2631543 | 11/1989 | France | ................................. 623/23 |
| 2640497 | 6/1990 | France | ................................. 623/22 |

*Primary Examiner*—John G. Weiss
*Assistant Examiner*—P. Zuttarelli
*Attorney, Agent, or Firm*—Cesari and McKenna, LLP

[57] ABSTRACT

A modular prosthesis allows two portions to be secured together with a selectable discrete relative angular orientation. A spline secured to one portion has projections which engage grooves in a cavity of the other portion to prevent angular motion between the portions. The spline and the cavity may be tapered to allow a pressure fit. Teeth secured to each portion may be used instead of a spline to secure the two portions in a selected discrete angular orientation. Alternatively, a pin may secure the portions together to prevent their relative angular movement. An additional securing means may also be used in combination with each of the above embodiments to further secure the two portions together.

27 Claims, 6 Drawing Sheets

MODULAR HIP PROSTHESIS WITH DISCRETE SELECTABLE ANGULAR ORIENTATION

BACKGROUND OF THE INVENTION

As hip replacement surgery becomes a more commonplace procedure in orthopedic medicine, there has been increasing focus on the design of the hip prostheses used. Due to the wide variation in bone structure from patient to patient and the wide array of clinical problems encountered, it is necessary to have prostheses of a number of different shapes and sizes. To address this problem, various modular designs comprised of two or more components have become popular. Use of such modular designs removes the need for keeping a vast inventory of one-piece hip prostheses and increases the options available to the surgeon during surgery.

Some previous two-piece modular hip prostheses have used wedges or sleeves which interconnect two parts of a prosthesis at the metaphyseal region. While such designs have provided an adequate connection for the modular prosthesis components, a medical risk exists to the recipient. The use of such sleeves and wedges inside the femoral canal raises the possibility of metal wear at the interface between the sleeve or wedge components from motion of the components relative to each other. Such metal wear may result in debris accumulating in the region of the patient's body containing the prosthesis, perhaps long after the surrounding bone has grown around it.

SUMMARY OF THE INVENTION

A hip prosthesis of the present invention has a stem portion and a neck portion securable to the stem portion by a fitting providing discrete selectable angular orientations of the neck portion relative to the stem portion. In one embodiment, the fitting comprises a spline which mates with a cavity which matches the shape of the spline. An outer surface of the spline is tapered and has projections equally disposed about it. The cavity is tapered to match the spline and has grooves disposed about an inner surface which receive the projections of the spline to prevent relative angular motion of the spline in the cavity. A pressure fit between the spline and the cavity due to the taper creates a high friction pressure fit, and holds the neck portion and the stem portion together.

The projections of the spline have a generally triangular cross-sectional shape. The grooves of the cavity may outnumber the projections, as long as the angular spacing between adjacent projections is a multiple of the angular spacing between adjacent grooves. This allows for ease of manufacture as the spline may be manufactured with fewer projections.

In another embodiment of the invention, the fitting comprises stem teeth rigidly secured to the stem portion and neck teeth rigidly secured to the neck portion. The stem teeth mesh with the neck teeth when the stem portion and the neck portion are brought into engagement with each other. Preferably, the stem teeth are equally spaced in a circular arrangement and the neck teeth are equally spaced in a circular arrangement having the same diameter as the circular arrangement of the stem teeth. As in the previous embodiment, it is preferable to have the angular spacing between adjacent neck teeth be a multiple of the angular spacing between adjacent stem teeth.

This embodiment may also have a male element and a female element which are mated when the neck portion and the stem portion are brought into engagement with each other. The male element may be located on either the neck portion or the stem portion, provided the female element is located on the other portion opposite the male element. Preferably, the circular arrangement of teeth of each of the stem portion and the neck portion surrounds either the male element or the female element. Furthermore, the male and female element may comprise a Morse Standard tapered fitting. In such a case the male element has the shape of a truncated cone and the female element a similar shape such that an outer surface of the male element resides in firm engagement with an inner surface of the female element to create a secure pressure fit when the stem portion is brought into engagement with the neck portion.

An additional embodiment of the present invention includes a fitting according to either of the two previous embodiments as well as an additional securing means for rigidly securing the neck portion to the stem portion. This securing means functions independently of the fitting, and may comprise a shaft having screw threads such as a bolt or screw. Preferably, the shaft is restricted to the neck portion and may be rotated into engagement with the stem portion to secure the neck portion to the stem portion.

A further embodiment uses at least one pin rigidly secured to the stem portion and holes in the neck portion each sized to receive the pin when the stem portion and the neck portion are brought into engagement with each other. There may also be a plurality of pins equally distributed in a circular arrangement which has the same diameter as a circular arrangement of the holes on the opposing portion. Similar to previous embodiments, there may be fewer pins than holes, with the angular spacing between adjacent pins being a multiple of the angular spacing between holes. There may also be a fitting having male and female elements on the stem and neck portions, which are mated when the stem portion and neck portion are brought into engagement with each other.

In a variation of this embodiment, each of the neck and stem portions may have holes which are aligned opposite one another when the portions are brought into engagement with each other. In such a case, pins are provided separately, each pin fitting in opposing holes of the stem and neck portion simultaneously. If holes on one of the two portions are not equally spaced at angular positions, but have angular separations from adjacent holes which are multiples of the angular spacing of adjacent holes on the opposing portion, a variety of different angular combinations is possible between the two portions. Indeed, the holes may be spaced to anticipate any predetermined positioning likely to be required.

BRIEF DESCRIPTION OF THE DRAWINGS

For a fuller understanding of the nature of the invention, reference should be had to the following detailed description taken in connection with the accompanying drawings, in which.

DETAILED DESCRIPTION OF THE PREFERRED EMBODIMENTS

Figure 1:
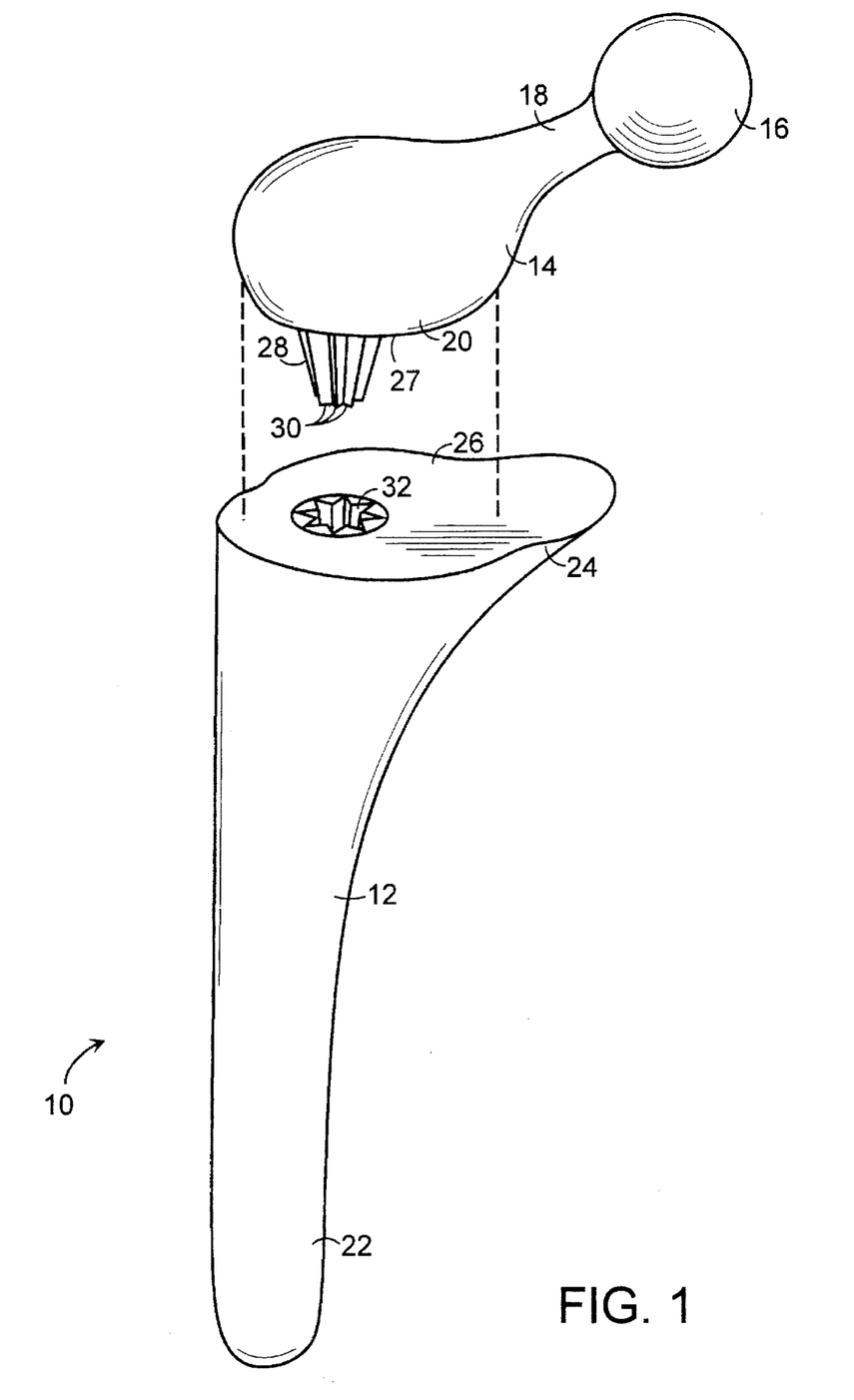
FIG. 1 is a perspective view of a hip prosthesis according to the present invention.

In accordance with the present invention, FIG. 1 shows, in perspective, a two-piece modular hip prosthesis generally indicated at 10. The prosthesis has two portions, a stem portion 12 and a neck portion 14. The neck portion 14 consists of a modular or fixed head 16 which fits into the patient's acetabulum or an artificial acetabulum, and a neck region 18 which tapers to a wider shoulder portion 20.

Figure 2:
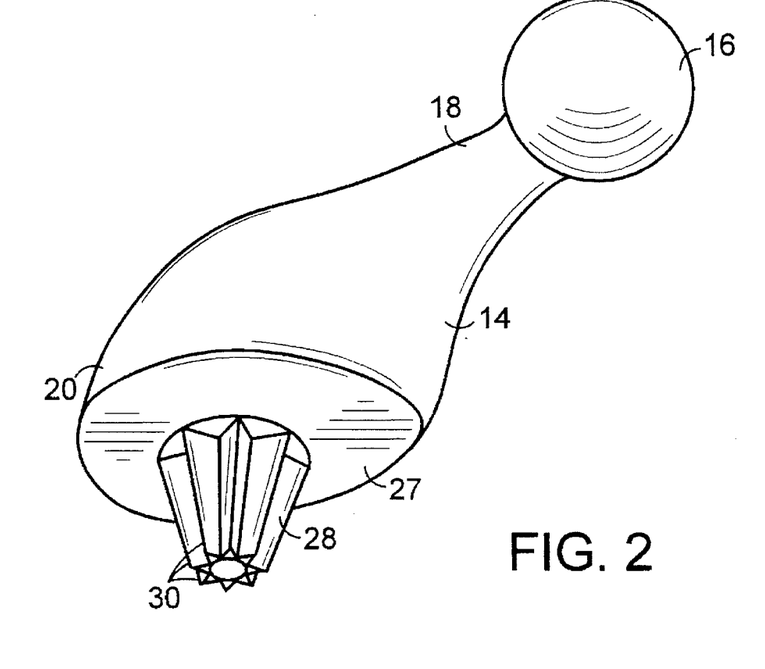
FIG. 2 is a perspective view of a neck portion of the prosthesis of FIG. 1.

The stem portion 12 of the hip prosthesis has a narrow shaft 22 which is rigidly secured to the patient's femur. The shaft 22 tapers along the length of the stem portion 12 to the metaphyseal flare 24. At the metaphyseal flare 24 the stem portion has a flat surface 26 which abuts flat surface 27 (better shown in FIG. 2) of neck portion 14. As shown in FIG. 2, integral with the flat surface 27 is a tapered spline 28 which has the shape of a truncated cone with angular projections 30 extending outwardly therefrom. In this embodiment, the projections 30 are equally spaced about the spline 28 and follow its taper. The projections 30 have a generally triangular cross-section, the area of which decreases away from the surface 27. It will be understood that the equal spacing of the projections 30 about the spline 28 are such that a cross-section of the spline parallel with surface 27 is "star-shaped" and the spline is radially symmetric about an axis perpendicular to surface 27 which passes through the center of the spline 28.

Figure 3:
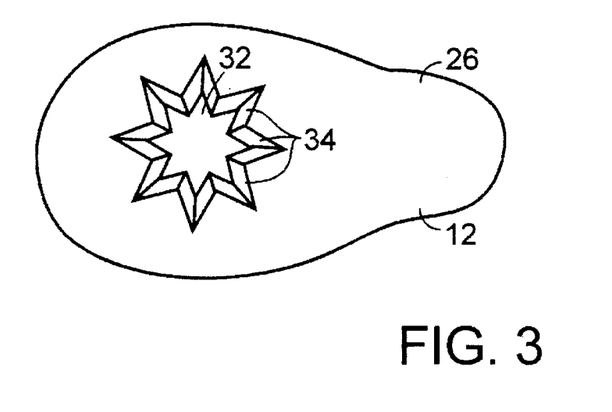
FIG. 3 is a top view of a stem portion of the hip prosthesis of FIG. 1.

The spline 28 is the male portion of a male/female connector which holds together the stem portion 12 and the neck portion 14 of the hip prosthesis 10. As such, the stem portion 12 has a female counterpart to spline 28 in the form of a tapered cavity 32 in flat surface 26. The tapered cavity 32 is better shown in FIG. 3 which is a top view of stem portion 12. As shown, the cavity 32 is recessed into the body of stem portion 12 and has the shape of a truncated cone with grooves 34 equally spaced about it. A cross-section of the cavity 32 parallel with surface 26 is "star-shaped" and the cavity 32 is preferably radially symmetric about an axis perpendicular to surface 26 which passes through the center of the cavity 32, although various angles of the spline and cavity relative to the surfaces 26, 27 are possible. The taper of the cavity 32 is such that the area of the cross-section decreases away from surface 26, while retaining the above-mentioned symmetry.

Referring back to FIG. 1, when stem portion 12 is brought into abutment with neck portion 14, spline 28 enters the cavity 32 and the projections 30 mesh with the grooves 34. The spline 28 is sized relative to the cavity 32 such that its outer surface engages the inner surface of cavity 32 and creates a tight pressure fit from friction between the spline and the cavity. In this position, surfaces 26 and 27 are slightly separated to avoid any wear between them and resulting debris. The extension of projections 30 into grooves 32 prevents any relative angular motion between neck portion 14 and stem portion 12 about an axis perpendicular to surfaces 26 and 27. This reduces the possibility of rotational failure of the components and may reduce debris accumulation from metal wear due to abrasion between the surfaces of spline 28 and cavity 32. The precision sizing and shaping of spline 28 and cavity 32 also create a pressure fit tight enough to resist lateral stresses between the stem portion 12 and the neck portion 14 as well as angular stresses about axes other than those perpendicular to surfaces 26 and 27.

When using the invention according to the embodiment of FIG. 1, stem portions 12 of different sizes and shapes can be connected with neck portions 14 of different sizes and shapes to create a myriad of different possible hip prostheses. Obviously, this is highly beneficial for obtaining the correct prosthesis for a particular patient. In addition, the structure of spline 28 and cavity 32 allow any one of a number of different discrete angular orientations between stem portion 12 and neck portion 14. Since different relative orientations may be correct for different patients, this allows the proper orientation for a particular patient to be determined and the prosthesis to be assembled at that correct relative orientation. The maximum number of possible discrete orientations is limited only by the number of projections 30 or grooves 34 on the spline 28 or in the cavity 32, respectively. It will be understood that the projections 30 and grooves 34 shown in the Figures are for diagrammatic purposes only, and that, in practice, the invention may have any number of projections 30 or grooves 34.

Figure 4:
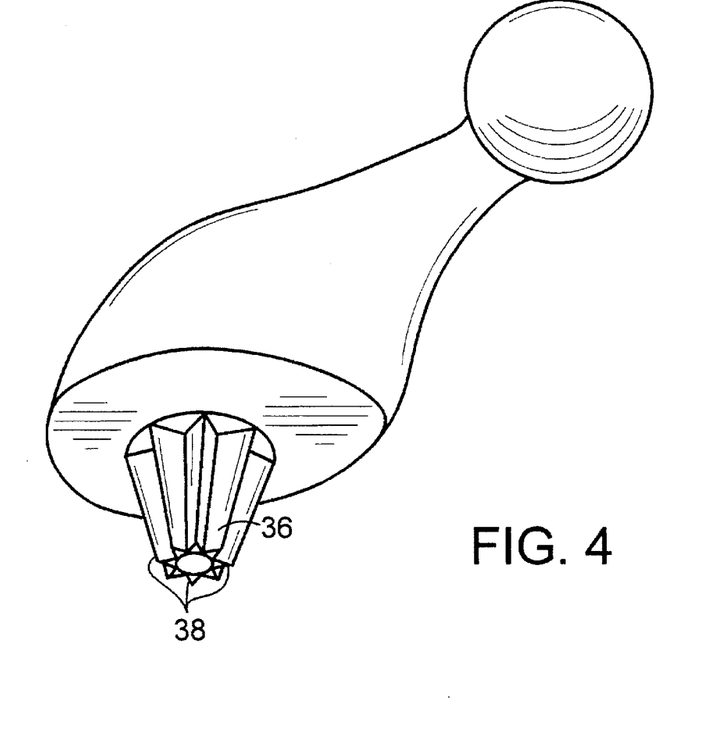
FIG. 4 is a perspective view of a neck portion of an alternative embodiment of the hip prosthesis of FIG. 1.

Since the projections 30 and the grooves 34 in this embodiment are radially symmetric about an axis perpendicular to surfaces 26 and 27, each discrete angular position will be x degrees from the two adjacent angular positions, where x=360° divided by the number of available discrete positions. In a related embodiment, it is not necessary for the number of projections 30 on spline 28 to equal the number of grooves 34 in cavity 32. Keeping the projections 30 sized to fit within grooves 34, fewer projections 30 may be used with similar results achieved. As long as the angular separation in degrees of adjacent projections 30 is a multiple of the angular separation of adjacent grooves 34, the possible number of relative angular orientations between stem portion 12 and neck portion 14 will equal the number of grooves 34. This embodiment is demonstrated by FIG. 4 which shows a tapered spline 36 having four projections 38. With the projections 38 being spaced equally around the body of the spline 36, each projection 38 has a relative separation of 90° from its adjacent projections. If spline 36 were inserted into cavity 32 of the stem in FIG. 3, eight different angular orientations would be available. Because the grooves 34 of cavity 32 are equally spaced at intervals of 45°, there are also grooves spaced 90° from each other for receiving the projections 38 in any one of eight different angular orientations.

Figure 5:
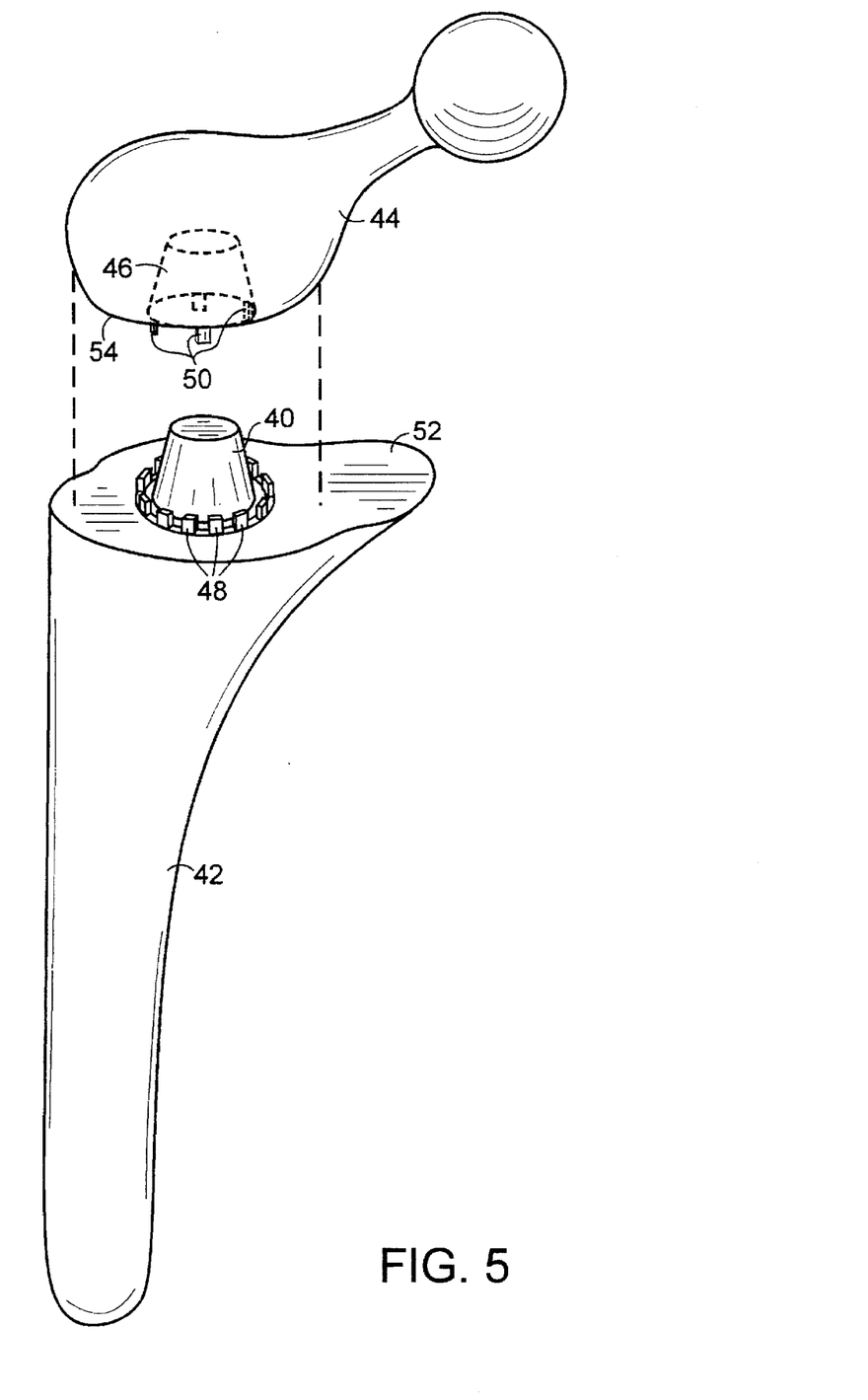
FIG. 5 is a perspective view of another alternative embodiment of the hip prosthesis of FIG. 1.

FIG. 5 is a perspective view of an alternative embodiment of the invention. Tapered stud 40 extends from the top surface of stem portion 42 of a hip prosthesis similar to that in FIG. 1. Neck portion 44 of the prosthesis has a tapered cavity 46 which is the female portion of the junction between stem portion 42 and neck portion 44, and which receives stud 40.

The first variation present in this embodiment applies to all male/female type junctions according to the invention, including that of FIG. 1. This variation has the male element 40 secured to the stem portion 42 of the prosthesis, while the female element 46 is within the neck portion 44 of the prosthesis. It will be understood that with all embodiments of the invention, the placing of the male and female elements of the fitting on either the stem portion 42 or the neck portion 44 is a matter of design choice. In the preferred embodiment of FIG. 1, the cavity 32 is located in the stem portion 12 because its volume is greater than that of neck portion 14. This provides more area within which to locate the cavity 32 and less chance of cracking or other failure of the material surrounding cavity 32.

A second aspect of the embodiment of FIG. 5 is the use of stem teeth 48 and neck teeth 50 which mesh with one another when cavity 46 is mated with stud 40. The stud 40 and the cavity 46 are sized and shaped to match each other so that when mated, a tight pressure fit will be formed due to the engagement of the tapered surface of stud 40 with the tapered surface surrounding cavity 46. In this embodiment, each of the stud 40 and the cavity 46 have the shape of a truncated cone. Stem teeth 48 are equally spaced and radially symmetric about an axis perpendicular to surface 52 and neck teeth are equally spaced and radially symmetric about an axis perpendicular to surface 54. The surfaces 52, 54 are flat surfaces of the stem portion 42 and neck portion 44, respectively, which are functionally equivalent to the flat surfaces 26 and 27 shown in FIGS. 1, 2 and 3.

When stud 40 is mated with cavity 46, teeth 50 mesh with teeth 48, preventing any relative angular movement between stem portion 42 and neck portion 44 about an axis perpendicular to surfaces 52, 54. As in the previous embodiments, any one of a number of different discrete angular orientations may be selected when assembling stem portion 42 and neck portion 44. Also as in the previous embodiments, the same limitations on the number of possible discrete orientations exist based on the number of teeth 48 or teeth 50. There may be more stem teeth 48 than neck teeth 50 or, alternatively, more neck teeth 50 than stem teeth 48. Due to the reciprocal intermeshing of teeth 48, 50, either arrangement would suffice. Furthermore, as in the previous embodiment, either the stem portion 42 or the neck portion 44 may have fewer teeth than the other, provided that the angular spacing between adjacent teeth on the portion having fewer teeth is a multiple of the angular spacing between adjacent teeth on the portion having the greater number of teeth.

Figure 6:
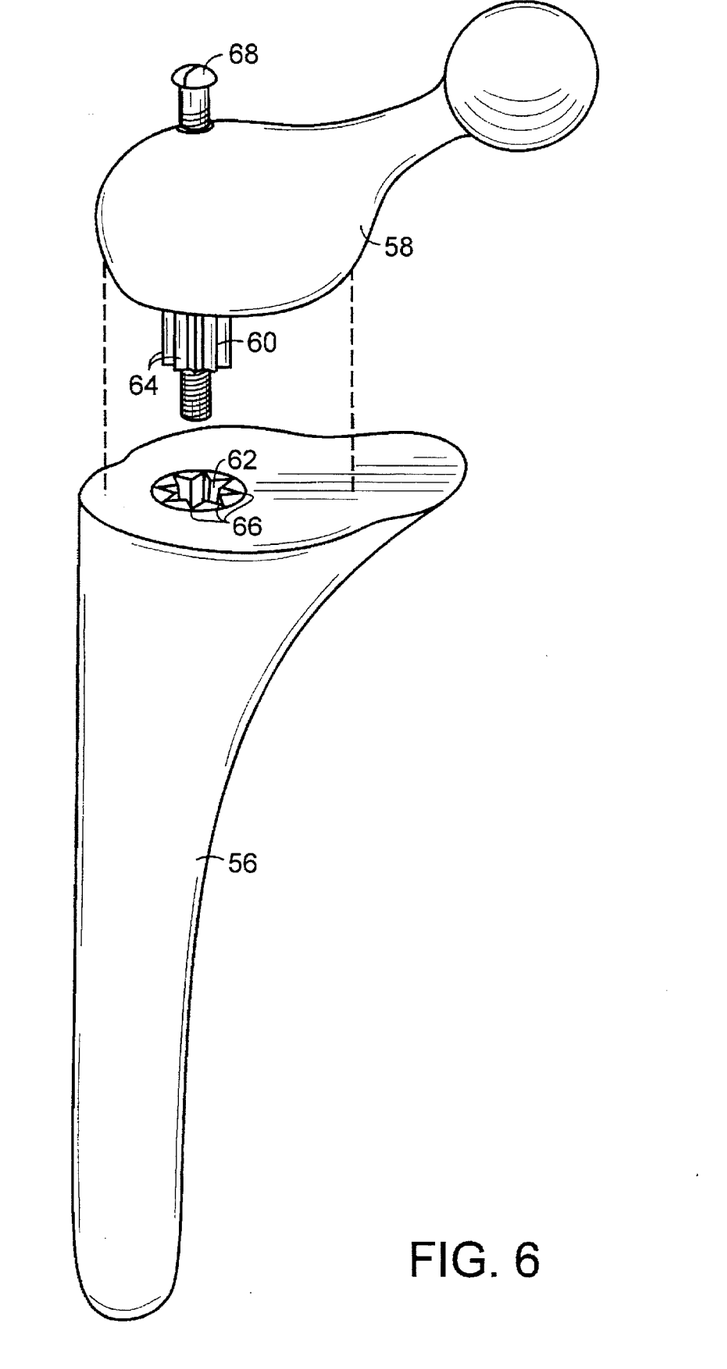
FIG. 6 is a perspective view of a further alternative embodiment of the hip prosthesis of FIG. 1.
Figure 7:
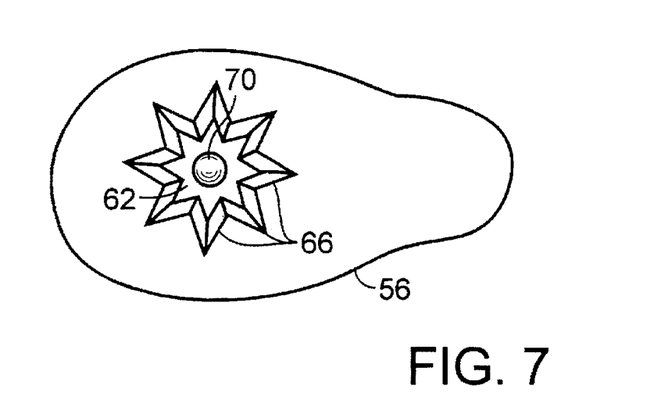
FIG. 7 is a top view of a stem portion of the hip prosthesis of FIG. 6.

FIG. 6 is a perspective view of a further embodiment of the present invention. A stem portion 56 and a neck portion 58 of a hip prosthesis similar to that of FIG. 1 use a fitting consisting of spline 60 and cavity 62 which are mated together upon assembly of the prosthesis. Unlike the embodiment of FIG. 1, however, the spline 60 and cavity 62 have a generally cylindrical shape rather than that of a truncated cone. Spline 60 has angular projections 64 which mesh with grooves 66 of cavity 62, providing the same discrete angular orientation selection as the embodiment of FIG. 1. However, instead of a pressure fit, the embodiment of FIG. 6 is secured by a securing means which in the preferred embodiment takes the form of bolt 68. The bolt 68 passes through the body of neck portion 58 and through the center of spline 60 and into threaded hole 70, which is better shown in FIG. 7. When the desired discrete angular orientation is selected, the spline 60 of neck portion 58 is mated with the cavity 62 of stem portion 56 to provide that orientation. Neck portion 58 is then rigidly secured to stem portion 56 by turning bolt 68 so that its threads mesh with the threads of threaded hole 70 until the portions 56, 58 are in tight engagement with each other.

It will be understood by those skilled in the art that the securing means of FIG. 6 may also take the form of a screw, a latch or any other known securing means. An adhesive material may also be used alone or in combination with the other securing means described. Furthermore, securing means independent of the fitting, such as that of FIG. 6, may also be used in conjunction with the tapered male/female fittings to provide both a pressure fit and an additional securing means. It should also be apparent that the bolt may be located on the stem portion 56 and may engage a threaded hole in the neck portion 58.

Figure 8:
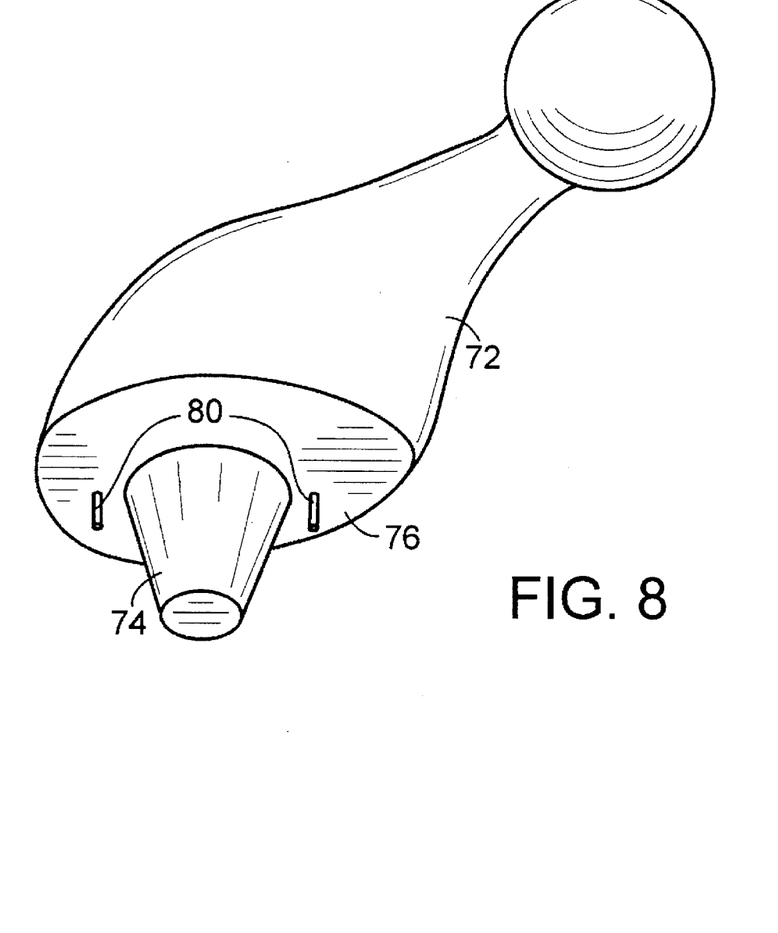
FIG. 8 is a perspective view of a neck portion of a still further alternative embodiment of the hip prosthesis of FIG. 1.
Figure 9:
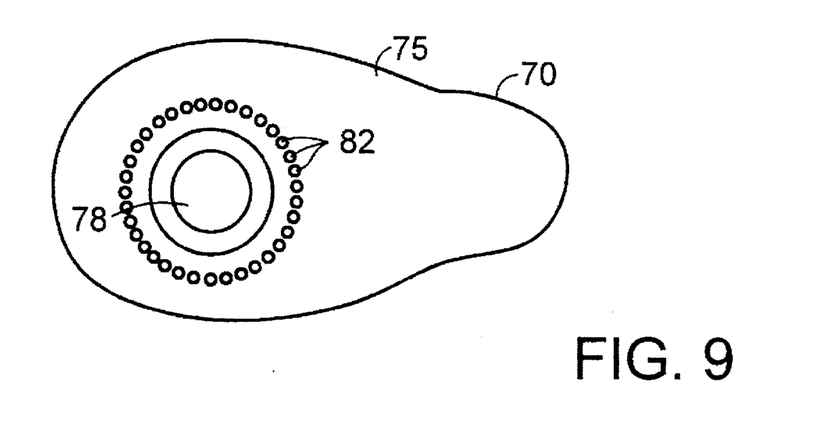
FIG. 9 is a top view of a stem portion of the hip prosthesis of FIG. 8.

FIG. 8 and FIG. 9 show an embodiment of the present invention which allows for ease of manufacture. FIG. 8 shows a perspective view of neck portion 72 which is similar to the perspective view of neck portion 14 in FIG. 2. FIG. 9 shows a top view of stem portion 70 which is similar to the top view of stem portion 12 shown in FIG. 3. The neck portion has a tapered stud 74 which extends from flat surface 76. The stud 74 mates with cavity 78 of stem portion 70 forming a tight pressure fit when portions 70 and 72 are brought into engagement with each other.

Adjacent stud 74 are pins 80 which are rigidly secured to flat surface 76. When stem portion 70 is brought into engagement with neck portion 72, each of pins 80 enters one of receiving holes 82 which are equally distributed in a circular arrangement around cavity 78. Once the pins 80 have been located in the desired receiving holes 82, they prevent any relative angular motion between stem portion 70 and neck portion 72 about an axis perpendicular to surfaces 75, 76. Furthermore, as in previous embodiments, having a plurality of equally spaced holes 82 around cavity 78 allows the selection of any one of a number of different discrete angular orientations determined by which holes 82 receive pins 80. In the embodiment shown in FIGS. 8 and 9, 36 equally spaced holes 82 allow for 36 different discrete angular orientations between stem portion 70 and neck portion 72, each ten degrees from the adjacent angular positions. However, any number of drive holes and pins may be used provided the pins are in a circular arrangement about stud 74, each having an angular spacing from adjacent pins which is a multiple of the angular spacing between adjacent holes 82. In a variation of this embodiment, the pins may be separate from both portions 70, 72, with holes being present in both portions. The holes may be equally spaced in both portions 70, 72, equally spaced in one portion with opposing holes spaced at varying angular positions in the other portion, or even unequally spaced in both portions 70, 72. Provided at least one hole of each portion oppose each other when the portions 70, 72 are joined together, a pin may be placed to fit in both simultaneously. This allows the angular orientation to be selected and the pins inserted by the person assembling the prosthesis. The variety of hole placement on both portions also allows various angular incremental differences between relative rotational positions of the portions 70, 72, as well as the ability to provide those relative positions which may be anticipated as being required. This feature would also greatly simplify manufacture of the pin-based prosthesis embodiment.

It will be understood that, as in the previous embodiments, the stud 74 may be located on stem portion 70 and the cavity on neck portion 72. The pins may be located on either stem portion 70 or neck portion 72, with the holes located on the opposite portion, or separate from both portions 70, 72. Furthermore, the features of this embodiment may be combined with the additional securing means 68 of FIG. 6 or with the tapered spline 28 of FIG. 1 without exceeding the scope of the present invention.

What is claimed is:

1. A modular hip prosthesis comprising:
   a first portion including a tapered stud having an outer surface;
   a second portion including a tapered cavity defined by an inner cavity surface which is sized to receive said tapered stud;

means for securing said first portion to said second portion to provide discrete selectable angular orientations of said second portion relative to said first portion and for reducing angular motion between said first and second portions; and wherein said tapered stud is inserted into said tapered cavity to rigidly secure the second portion to the first portion by means of friction pressure between said outer surface and said inner cavity surface.

2. A prosthesis according to claim 1 wherein the prosthesis is a hip prosthesis.

3. A prosthesis according to claim 1 wherein said means for securing comprises at least one pin which is separate from the first portion and the second portion and which resides simultaneously in a hole in a surface of the first portion and a hole in a surface of the second portion when the second portion and the first portion are brought into engagement with each other.

4. The modular prosthesis of claim 1 wherein said first portion is a prosthetic stem and said second portion is a prosthetic neck.

5. The modular prosthesis of claim 1 wherein said first portion is a prosthetic neck and said second portion is a prosthetic stem.

6. A prosthesis according to claim 1 wherein said means for securing comprises a plurality of projections disposed about said outer surface and each of which mates with one of a plurality of grooves formed in and disposed around said inner cavity surface.

7. A prosthesis according to claim 6 wherein said plurality of projections are disposed about said inner cavity surface at equal angular intervals.

8. A prosthesis according to claim 7 wherein the projections have a generally triangular cross-sectional shape.

9. A prosthesis according to claim 7 wherein the grooves outnumber the projections.

10. A prosthesis according to claim 1 wherein said means for securing comprises primary teeth rigidly secured to the first portion and secondary teeth rigidly secured to the second portion which mesh with the primary teeth when the first portion and the second portion are brought into engagement with each other.

11. A prosthesis according to claim 10 wherein the primary teeth are disposed in a circular arrangement about the tapered stud and the secondary teeth are disposed in a circular arrangement about the tapered cavity.

12. A prosthesis according to claim 10 wherein the tapered stud has the shape of a truncated cone.

13. A prosthesis according to claim 10 wherein the primary teeth are equally spaced in a circular arrangement and the secondary teeth are equally spaced in a circular arrangement having the same diameter as the circular arrangement of the primary teeth.

14. A prosthesis according to claim 13 wherein the angular spacing between adjacent secondary teeth is a multiple of the angular spacing between adjacent primary teeth.

15. A prosthesis according to claim 1 wherein said means for securing comprises at least one pin rigidly secured to the first portion and a plurality of holes spaced around and outside of said tapered cavity wherein each of said plurality of holes is sized to receive said pin when the first portion and the second portion are brought into engagement with each other.

16. A prosthesis according to claim 15 wherein there is a plurality of said pins which are equally distributed in a circular arrangement and wherein the holes on the second portion are equally distributed in a circular arrangement having the same diameter as the circular arrangement of the pins.

17. A prosthesis according to claim 16 wherein the angular spacing between the adjacent pins is a multiple of the angular spacing between adjacent holes.

18. A prosthesis according to claim 16 wherein the fitting further comprises a male element and a female element which are mated when the second portion and the first portion are brought into engagement with each other.

19. A method for producing a customized prosthesis comprising the steps of:
   selecting a stem portion comprising a tapered stud having an outer surface;
   selecting a neck portion comprising a tapered cavity defined by an inner cavity surface which is sized to receive said tapered stud;
   selecting one of a plurality of discrete relative angular orientations at which to join the stem portion and the neck portion; and
   securing said portions together by inserting said tapered stud into said tapered cavity to rigidly secure the second portion to the first portion at the selected discrete relative angular orientation by means of friction pressure between said outer surface and said inner cavity surface.

20. A method according to claim 19 wherein producing a customized prosthesis comprises producing a customized hip prosthesis.

21. A method of producing a customized hip prosthesis comprising the steps of:
   selecting a stem portion comprising a tapered cavity defined by an inner cavity surface which is sized to receive said tapered stud;
   selecting a neck portion comprising a tapered stud having an outer surface;
   selecting one of a plurality of discrete relative angular orientations between the stem portion and the neck portion; and
   securing said portions together by inserting said tapered stud into said tapered cavity to rigidly secure the second portion to the first portion at the selected discrete relative angular orientation by means of friction pressure between said outer surface and said inner cavity surface.

22. A modular hip prosthesis, comprising:
   a stem portion which includes a narrow shaft which is rigidly mounted to a patient's femur, said stem portion includes a metaphyseal flare and a flat surface atop said metaphyseal flare, wherein a tapered cavity defined by a tapered inner surface is formed in said top surface and said tapered inner surface includes a plurality of equally spaced grooves disposed around said inner surface; and
   a neck portion which is tapered from a narrow end to a second end which is thicker than said narrow end, wherein said second end includes a flat neck surface and a tapered spline having a spline outer surface that includes a plurality of equally spaced projections, said spline projects in a direction substantially perpendicular to said flat neck surface, wherein said stem portion and said neck portion are joined together by inserting said tapered spline into said tapered cavity so said spline outer surface forms a friction pressure fit with said cavity inner surface, and any of said projections can be mated with any of said grooves to provide a selectable one of a plurality of discrete relative angular orientations of said stem portion with respect to said neck portion, and to reduce angular motion between said stem and neck portions.

23. A modular hip prosthesis, comprising:
   a stem portion which includes a narrow shaft which is rigidly mounted to a patient's femur, said stem portion includes a metaphyseal flare and a flat surface atop said metaphyseal flare, wherein a tapered spline is formed on said top surface and defined by a spline outer surface that includes a plurality of equally spaced projections, said spline projects in a direction substantially perpendicular to said flat surface; and a neck portion which is tapered from a narrow end to a second end which is thicker than said narrow end, wherein said second end includes a flat neck surface and a tapered cavity formed in said flat neck surface and defined by a tapered inner surface, said tapered inner surface includes a plurality of equally spaced grooves disposed around said inner surface, wherein said stem portion and said neck portion are joined together by inserting said tapered spline into said tapered cavity so said spline outer surface forms a friction pressure fit with said cavity firmer surface, and any of said projections can be mated with any of said grooves to provide a selectable one of a plurality of discrete relative angular orientations of said stem portion with respect to said neck portion, and to reduce angular motion between said stem and neck portions.

24. A modular hip prosthesis, comprising:

a stem portion which includes a narrow shaft which is rigidly mounted to a patient's femur, said stem portion includes a metaphyseal flare and a flat surface atop said metaphyseal flare, and a tapered cavity defined by a tapered inner surface formed in said top surface, wherein said top surface also includes a plurality of stem teeth arranged at a certain diameter around said tapered cavity; and a neck portion which is tapered from a narrow end to a second end which is thicker than said narrow end, wherein said second end includes a flat neck surface and a tapered stud having a stud outer surface, said stud projects in a direction substantially perpendicular to said flat neck surface, wherein said stem portion and said neck portion are joined together by inserting said tapered stud into said tapered cavity so said stud outer surface forms a friction pressure fit with said cavity inner surface, and said flat neck portion also includes a plurality of neck teeth arranged around said tapered stud in a diameter equal to said fixed diameter, wherein any of said stem teeth can mate with any of said neck teeth to provide a selectable one of a plurality of discrete relative angular orientations of said stem portion with respect to said neck portion, and to reduce angular motion between said stem and neck portions when said stem portion and said neck portion are joined together.

25. A modular hip prosthesis, comprising:

a stem portion which includes a narrow shaft which is rigidly mounted to a patient's femur, said stem portion includes a metaphyseal flare and a flat surface atop said metaphyseal flare, wherein a tapered stud is formed on said top surface and defined by a stud outer surface which projects in a direction substantially perpendicular to said flat surface, said stem portion also comprising a plurality of stem teeth arranged at a certain diameter around said tapered stud; and a neck portion which is tapered from a narrow end to a second end which is thicker than said narrow end, said second end includes a flat neck surface and a tapered cavity formed in said flat neck surface and defined by a tapered inner surface, wherein said flat neck surface also includes a plurality of stem teeth arranged around said tapered cavity at a diameter equal to said certain diameter, wherein said stem portion and said neck portion are joined together by inserting said tapered stud into said tapered cavity so said stud outer surface forms a friction pressure fit with said cavity inner surface, and any of said stem teeth can be mated with any of said neck teeth to provide a selectable one of a plurality of discrete relative angular orientations of said stem portion with respect to said neck portion, and to reduce angular motion between said stem and neck portions when said stem and neck portions are joined together.

26. A modular hip prosthesis, comprising:

a stem portion which includes a narrow shaft which is rigidly mounted to a patient's femur, said stem portion includes a metaphyseal flare and a flat surface atop said metaphyseal flare, wherein a tapered stud is formed on said top surface and defined by a stud outer surface that includes a plurality of equally spaced openings in said flat surface arranged in a certain diameter around and co-axial with said tapered stud; and a neck portion which is tapered from a narrow end to a second end which is thicker than said narrow end, wherein said second end includes a flat neck surface and a tapered cavity formed in said flat neck surface and defined by a tapered inner surface, said flat neck surface includes a plurality of equally spaced mating pins disposed around and co-axial with said tapered cavity, wherein said stem portion and said neck portion are joined together by inserting said tapered stud into said tapered cavity so said stud outer surface forms a friction pressure fit with said cavity inner surface, and any of said equally spaced mating pins can be mated with any of said equally spaced openings to provide a selectable one of a plurality of discrete relative angular orientations of said stem portion with respect to said neck portion, and to reduce angular motion between said stem and neck portions when said stem portion and said neck portion are joined together.

27. A modular hip prosthesis, comprising:

a stem portion which includes a narrow shaft which is rigidly mounted to a patient's femur, said stem portion includes a metaphyseal flare and a flat surface atop said metaphyseal flare, and a tapered cavity defined by a tapered inner surface formed in said top surface, wherein said top surface also includes a plurality of equally spaced openings arranged in a fixed diameter around and coaxial with said tapered cavity; and a neck portion which is tapered from a narrow end to a second end which is thicker than said narrow end, wherein said second end includes a flat neck surface and a tapered stud having a stud outer surface, said stud projects in a direction substantially perpendicular to said flat neck surface, wherein said stem portion and said neck portion are joined together by inserting said tapered stud into said tapered cavity so said stud outer surface forms a friction pressure fit with said cavity inner surface, and said neck portion includes a plurality of equally spaced mating pins arranged around and co-axial with said tapered stud in a diameter equal to said fixed diameter wherein any of said mating pins can mate with any of said equally spaced openings to provide a selectable one of a plurality of discrete relative angular orientations of said stem portion with respect to said neck portion, and to reduce angular motion between said stem and neck portions when said stem portion and said neck portion are joined together.

* * * * *